(12) United States Patent
Wang

(10) Patent No.: US 11,552,254 B2
(45) Date of Patent: Jan. 10, 2023

(54) THERMALLY ACTIVATED DELAYED FLUORESCENT MOLECULAR MATERIAL, A SYNTHESIZING METHOD THEREFOR, AND AN ELECTROLUMINESCENT DEVICE

(71) Applicant: WUHAN CHINA STAR OPTOELECTRONICS SEMICONDUCTOR DISPLAY TECHNOLOGY CO., LTD., Hubei (CN)

(72) Inventor: Yanjie Wang, Wuhan (CN)

(73) Assignee: WUHAN CHINA STAR OPTOELECTRONICS SEMICONDUCTOR DISPLAY TECHNOLOGY CO., LTD., Hubei (CN)

( * ) Notice: Subject to any disclaimer, the term of this patent is extended or adjusted under 35 U.S.C. 154(b) by 327 days.

(21) Appl. No.: 16/629,971

(22) PCT Filed: Oct. 24, 2019

(86) PCT No.: PCT/CN2019/112896
§ 371 (c)(1),
(2) Date: Feb. 10, 2020

(87) PCT Pub. No.: WO2020/237991
PCT Pub. Date: Dec. 3, 2020

(65) Prior Publication Data
US 2020/0381632 A1    Dec. 3, 2020

(30) Foreign Application Priority Data
May 27, 2019 (CN) .......................... 201910445244.3

(51) Int. Cl.
*H01L 51/00* (2006.01)
*C09K 11/06* (2006.01)
*C07D 517/04* (2006.01)
*H01L 51/50* (2006.01)

(52) U.S. Cl.
CPC ........ *H01L 51/0071* (2013.01); *C07D 517/04* (2013.01); *C09K 11/06* (2013.01); *H01L 51/0067* (2013.01); *C09K 2211/1007* (2013.01); *C09K 2211/1018* (2013.01); *H01L 51/5012* (2013.01); *H01L 51/5056* (2013.01); *H01L 51/5072* (2013.01); *H01L 51/5088* (2013.01); *H01L 2251/301* (2013.01); *H01L 2251/308* (2013.01)

(58) Field of Classification Search
CPC .............. C07D 517/04; H01L 51/0071; H01L 51/0067; H01L 51/5088; C09K 11/06
See application file for complete search history.

(56) References Cited

FOREIGN PATENT DOCUMENTS

| CN | 106467482 A | 3/2017 |
|----|-------------|--------|
| CN | 108358905 A | 8/2018 |
| CN | 110092800 A | 8/2019 |
| KR | 20140079315 A | 6/2014 |

OTHER PUBLICATIONS

Synthesis and Performance of Efficient Organic Phosphorescent Bipolar Host Materials.

*Primary Examiner* — Joseph R Kosack
*Assistant Examiner* — Sagar Patel
(74) *Attorney, Agent, or Firm* — PV IP PC; Wei Te Chung; Ude Lu

(57) ABSTRACT

A thermally activated delayed fluorescent molecular material, a synthesizing method therefor, and an electroluminescent device are provided. The thermally activated delayed fluorescent molecular containing an indenobenzoselenoheteroaromatic ring donor is synthesized, so that an electron donating ability of the donor is increased, and an nonradiative transition rate is effectively inhibited, thereby increasing photo-luminescence quantum yield (PLQY) of the molecule; and increasing the twist angle between the electron donor and the electron acceptor. Meanwhile, electron cloud overlapping between highest occupied molecular orbital (HOMO) and lowest unoccupied molecular orbital (LUMO) is reduced, thereby obtaining a smaller $\Delta E_{ST}$ value. The organic electroluminescent device adopts the thermally activated delayed fluorescent molecular material prepared according to the synthesizing method, and thus has high luminous efficiency and long service life.

2 Claims, 2 Drawing Sheets

THERMALLY ACTIVATED DELAYED FLUORESCENT MOLECULAR MATERIAL, A SYNTHESIZING METHOD THEREFOR, AND AN ELECTROLUMINESCENT DEVICE

FIELD OF INVENTION

The present invention relates to a field of display technologies, in particular, to a thermally activated delayed fluorescent molecular material, a synthetic method therefor, and an electroluminescent device.

BACKGROUND OF INVENTION

Organic light-emitting diodes (OLEDs) have advantages, such as self-illumination, wide viewing angles, fast response times, wide operation temperature ranges, low driving voltage, low power consumption, high brightness, simple manufacturing process, thinness, lightness, and flexible display, etc., there are great application prospects in OLED display and illumination field and attracting the attention of researchers and companies. Currently, SAMSUNG and LG have implemented OLEDs on mobile phones. In OLED, luminescent layer material quality is a decisive factor of OLED industrialization. Generally, a luminescent layer material is made of a main luminescent material and a subordinate luminescent material, and the luminescent efficiency and lifetime of the luminescent materials are two important indicators of the luminescent materials. Early OLED luminescent materials are traditional fluorescent materials. Because a ratio of singlet state and triplet state excitons in the OLED is 1:3, the traditional fluorescent materials can only use singlet state excitons luminescence. Therefore, a theoretical quantum efficiency of the traditional OLED fluorescent material is 25%. A metal complex phosphorescent material enables 100% utilization of singlet state excitons and triplet state excitons due to the spin-orbit coupling effect of heavy atoms; and it has also been used in green OLED displays. However, the phosphorescent materials usually use precious metals, such as heavy metals iridium(Ir), platinum (Pt), and osmium (Os), which are not only costly but also highly toxic. In addition, high efficient, long-life phosphorescent metal complex materials remain a significant challenge. In year 2012, Adachi et al. proposed a pure organic luminescent molecule with a "thermally activated delayed fluorescence" (TADF) mechanism. The molecule has a smaller energy level difference ($\Delta E_{ST}$) of minimum singlet state and triplet state by rational D(donor)-A (acceptor) structure molecular design. Such triplet state excitons can return to the singlet state through the reverse intersystem crossing (RISC), and then illuminate by radiation transition to the ground state, so that the singlet state and triplet state excitons can be simultaneously utilized, so that 100% excitons utilization can be achieved without the involvement of heavy metals. Moreover, TADF material structures are rich in design, and most of their physical properties are easily adjusted to obtain efficient, long-life organic luminescent materials that meet the requirements.

TECHNICAL PROBLEM: Most of TADF molecular designs are D (donor)-A(acceptor) type structures. Furthermore, the donors are usually diphenylamine, carbazole and acridine or a derivative structure thereof. The torsion angle of carbazole and the acceptor A is suitable, but the electron donating ability of carbazole is too weak; the electron donating ability of diphenylamine is moderate, but the torsion angle of diphenylamine and the acceptor A is too small; the electron donating ability of acridine is very strong, but the torsion angle of acridine and the acceptor is too large. Although the large torsion angle may make the RISC rate high, the photoluminescence quantum efficiency (PLQY) of the material may decrease; If the electron donating ability is too weak, which may make the electric charge transfer between D and A poor. The degree of overlap between highest occupied molecular orbit (HOMO) and lowest unoccupied molecular orbital (LUMO) between the donor and the acceptor is too large, resulting in a larger $\Delta E_{ST}$.

SUMMARY OF INVENTION

In order to solve the above technical problem, a thermally activated delayed fluorescent molecular material, a synthesizing method therefor, and an electroluminescent device are provided. The thermally activated delayed fluorescent molecular containing an indenobenzoselenoheteroaromatic ring donor is synthesized, so that an electron donating ability of the donor is increased, and an non-radiative transition rate is effectively inhibited, thereby increasing photo-luminescence quantum yield (PLQY) of the molecule; and increasing the twist angle between the electron donor and the electron acceptor. Meanwhile, electron cloud overlapping between highest occupied molecular orbital (HOMO) and lowest unoccupied molecular orbital (LUMO) is reduced, thereby obtaining a smaller $\Delta E_{ST}$ value. The organic electroluminescent device adopts the thermally activated delayed fluorescent molecular material prepared according to the synthesizing method, and thus has high luminous efficiency and long service life.

The technical solution to solve the above problems is: a thermally activated delayed fluorescent molecular material, including an electron donor and an electron acceptor, wherein the electron donor includes an indenobenzoselenoheteroaromatic ring structure.

Further, a structure of the electron donor includes one of the following structures:

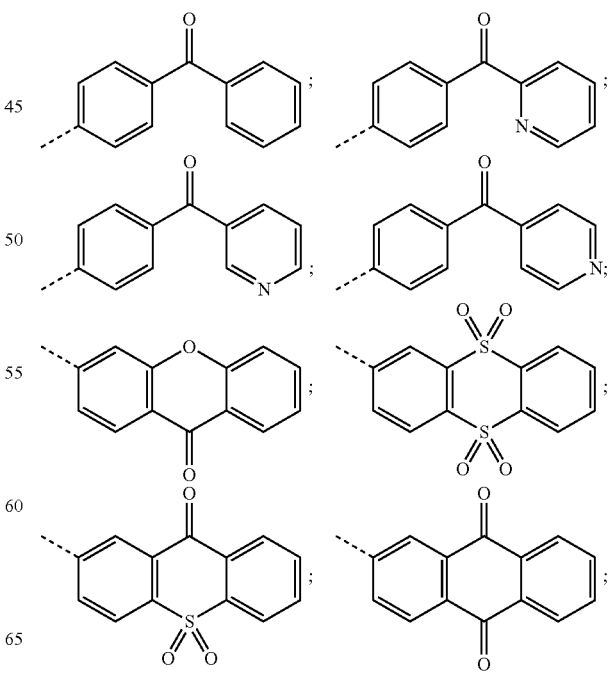

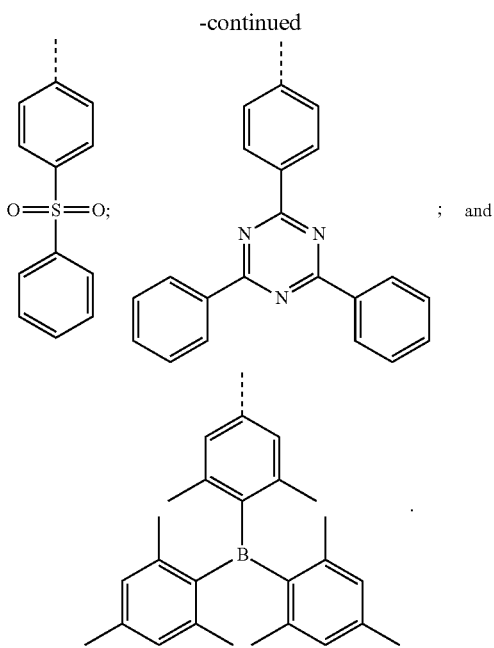

Further, a structure of the electron acceptor includes one of the following structures:

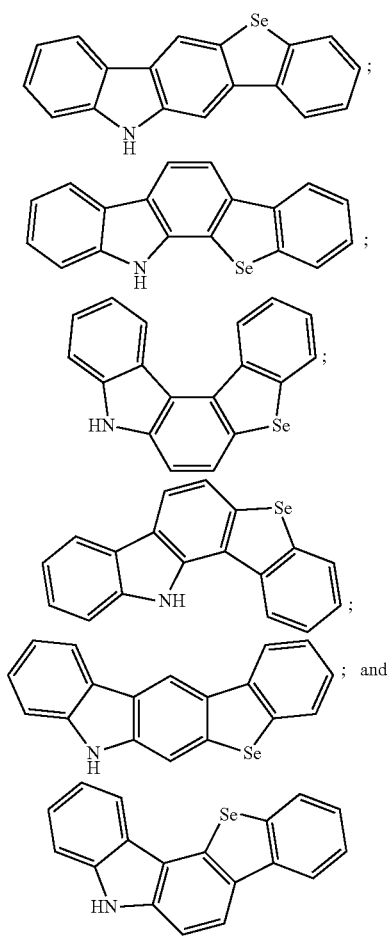

The present further provides a synthesizing method for a thermally activated delayed fluorescent molecular material, including steps of: providing an electron donor raw material containing an indenobenzoselenoheteroaromatic ring structure, an electron acceptor raw material, sodium tert-butoxide, and a catalyst in a reaction container, and pumping and exchanging air in the reaction container with argon; adding a solvent into the reaction container, performing a reflux reaction for 24 hours, and cooling to obtain a first mixed solution; performing three extractions of the first mixed solution with dichloromethane and three times of water washing, and performing drying with anhydrous sodium sulfate, filtering, and concentrating to obtain a target compound; and performing a column chromatography to the target compound solution by using silica gel having 200 to 300 meshes, and rinsing with an eluent, and finally isolating and purifying to obtain the thermally activated delayed fluorescent molecular material.

Further, the donor group raw material is 12H-phenyl[4,5]selenophene [3,2-a]carbazole; the acceptor group raw material is 2-(4-bromophenyl)-4,6-diphenyl-1,3,5-triazine, the catalyst includes tris(dibenzylideneacetone)dipalladium and tri-tert-butylphosphine tetrafluoroborate; a molar ratio of the donor group raw material, the acceptor group raw material, and the sodium tert-butoxide is 2:2:5; a molar ratio of the tris(dibenzylideneacetone)dipalladium to the tri-tert-butylphosphine tetrafluoroborate is 1:4; the solvent is anhydrous toluene; and the eluent is petroleum ether and dichloromethane.

The present invention yet provides an electroluminescent device, including a thermally activated delayed fluorescent molecular material.

Further, the electroluminescent device includes: a first electrode; a hole injection layer disposed on the first electrode; a hole transport layer disposed on the hole injection layer; a light-emitting layer disposed on the hole transport layer, wherein material of the light-emitting layer includes the thermally activated delayed fluorescent molecular material; an electron transport layer disposed on the light emitting layer; and a second electrode disposed on the electron transport layer.

Further, the light-emitting layer further includes 1,3-bis (9H-carbazol-9-yl)benzene.

Further, the first electrode is an anode, and material of the first electrode is indium tin oxide; and the second electrode is a cathode, and material of the second electrode is one of lithium fluoride or aluminum.

Further, material of the hole injection layer is 2,3,6,7,10,11-hexacyano-1,4,5,8,9,12-hexaazatriphenylene; material of the electron transport layer is 1,3,5-tri(3-(3-pyridyl)phenyl)benzene, and material of the hole transport layer is 4,4'-cyclohexylidenebis [N,N-bis(4-methylphenyl)aniline].

BENEFICIAL EFFECT: A thermally activated delayed fluorescent molecular material, a synthesizing method therefor, and an electroluminescent device are provided. The thermally activated delayed fluorescent molecular containing an indenobenzoselenoheteroaromatic ring donor is synthesized, so that an electron donating ability of the donor is increased, and an non-radiative transition rate is effectively inhibited, thereby increasing photo-luminescence quantum yield (PLQY) of the molecule; and increasing the twist angle between the electron donor and the electron acceptor. Meanwhile, electron cloud overlapping between highest occupied molecular orbital (HOMO) and lowest unoccupied molecular orbital (LUMO) is reduced, thereby obtaining a smaller $\Delta E_{ST}$ value. The organic electroluminescent device adopts the thermally activated delayed fluorescent molecular material prepared according to the synthesizing method, and thus has high luminous efficiency and long service life.

DRAWINGS

In order to more clearly illustrate the technical solutions in the embodiments of the present invention, the drawings used in the description of the embodiments will be briefly described below. It is apparent that the drawings in the following description are only some embodiments of the present invention. Other drawings can also be obtained from those skilled in the art based on these drawings without paying any creative effort.

REFERENCE NUMERALS

Figure 1:
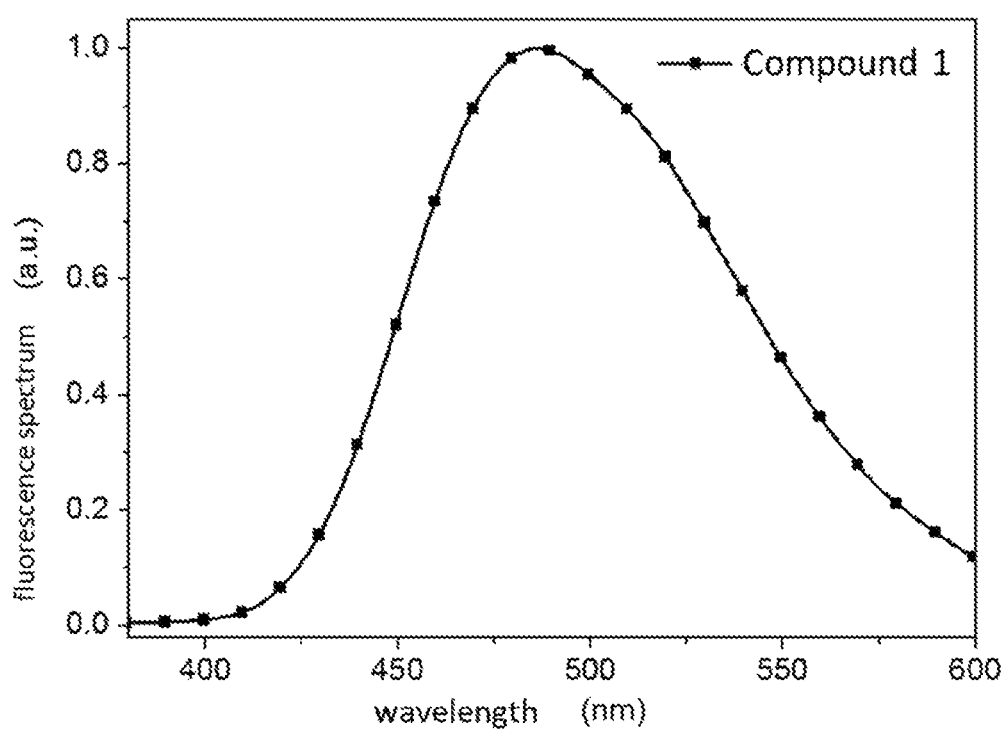
FIG. 1 is a fluorescence spectrum diagram of a thermally activated delayed fluorescent molecular material obtained by the preparation method of the present invention.

| 10 electroluminescent device; | |
|---|---|
| 1 first electrode; | 2 hole injection layer; |
| 3 hole transport layer; | 4 light-emitting layer; |
| 5 electron transport layer; | 6 second electrode. |

DETAILED DESCRIPTION OF EMBODIMENTS

The following description of the various embodiments is intended to be illustrative of the specific embodiments The directional terms mentioned in the present invention, such as upper, lower, front, rear, left, right, inner, outer, side, etc., are merely directions referring to the drawings. The names of the elements mentioned in the present invention, such as the first, second, etc., are only distinguishing between different components and can be better expressed. In the drawings, structurally similar elements are denoted by the same reference numerals.

Embodiments of the present invention will be described in detail herein in conjunction with the accompanying drawings. The present invention may be implemented in many different embodiments and the invention should not be construed as being limited to the specific embodiments set forth herein. The embodiments of the present invention are provided to explain the practical application of the present invention so that those skilled in the art can understand various embodiments of the present invention and various modifications suitable for the particular intended application.

The present invention provides a thermally activated delayed fluorescent molecular material, including an electron donor and an electron acceptor, wherein the electron donor includes an indenobenzoselenoheteroaromatic ring structure. The thermally activated delayed fluorescent molecular material has the following structures:

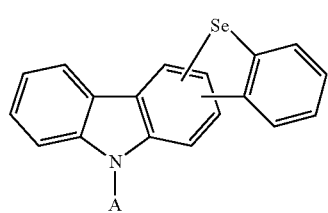

A structure of the electron donor includes one of the following structures:

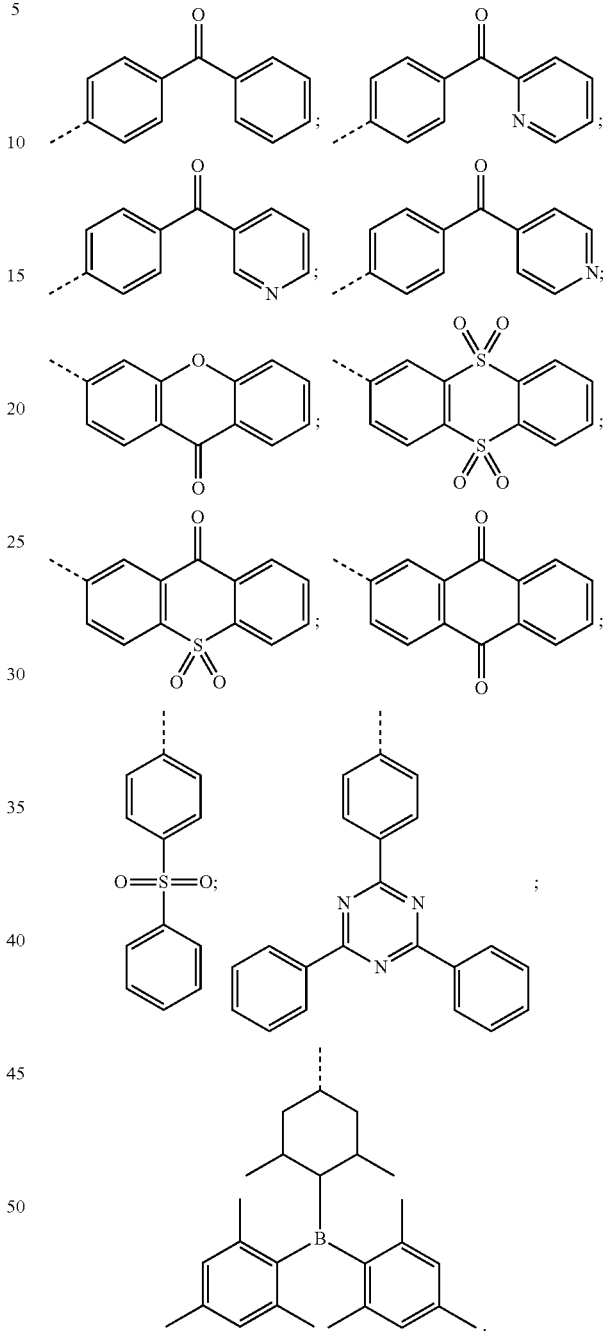

A structure of the electron acceptor includes one of the following structures:

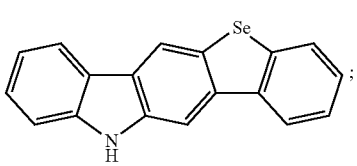

-continued

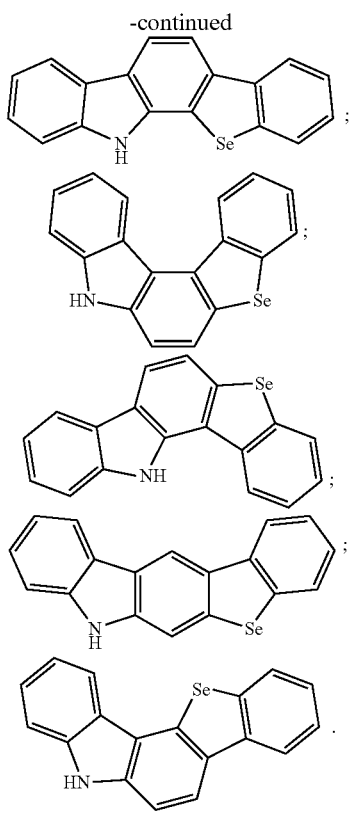

In order to more clearly explain the present invention, the thermally activated delayed fluorescent molecular material is further explained below in conjunction with a thermally activated delayed fluorescent molecular material synthesis method of the present invention.

In one embodiment of the present invention, a preparation method of the thermally activated delayed fluorescent molecular material according to the present invention will be described in detail by taking a target compound 1 preparation (a thermally activated delayed fluorescent molecular material according to the present invention) as an example. A structure of the target compound 1 is as follows:

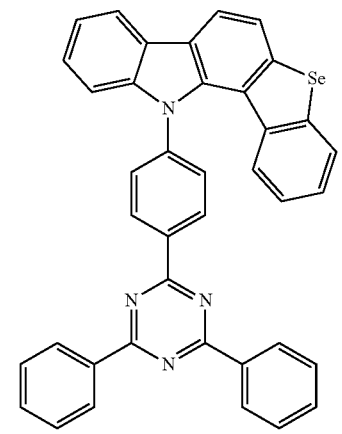 [SMILES: c1ccc(-c2nc(-c3ccccc3)nc(-c3ccc(-n4c5ccccc5c5ccc6[se]c7ccccc7c6c54)cc3)n2)cc1]

The preparation method of the thermally activated delayed fluorescent molecular material according to the present invention includes following steps:

A step S1 of providing a donor group raw material containing an indenobenzoselenoheteroaromatic ring structure, an acceptor group raw material, sodium tert-butoxide, and a catalyst in a reaction container, and pumping and exchanging air in the reaction container with argon.

The reaction container may be a 100 ml Schlenk bottle. The donor group raw material may be 12H-phenyl[4,5] selenophene [3,2-a]carbazole or 2-(4-bromophenyl)-4,6-diphenyl-1,3,5-triazine. The acceptor group raw material may be 2-(4-bromophenyl)-4,6-diphenyl-1,3,5-triazine. The catalyst may be tris(dibenzylideneacetone)dipalladium and tri-tert-butylphosphine tetrafluoroborate. A molar ratio of the donor group raw material, the acceptor group raw material, and the sodium tert-butoxide may be 2:2:5. A molar ratio of the tris(dibenzylideneacetone)dipalladium to the tri-tert-butylphosphine tetrafluoroborate is 1:4.

A step S2 of adding a solvent into the reaction container, performing a reflux reaction for 24 hours, and cooling to obtain a first mixed solution; the solvent is anhydrous toluene (40 mL).

A step S3 of performing three extractions of the first mixed solution with dichloromethane and three times of water washing, and performing drying with anhydrous sodium sulfate, filtering, and concentrating to obtain a target compound.

A step S4 of performing a column chromatography to the target compound solution by using silica gel having 200 to 300 meshes, and rinsing with an eluent, and finally isolating and purifying to obtain the thermally activated delayed fluorescent molecular material. The eluent may be petroleum ether and dichloromethane (4:1, V/V).

Through the preparation method of this embodiment, a specific chemical reaction equation is as follows:

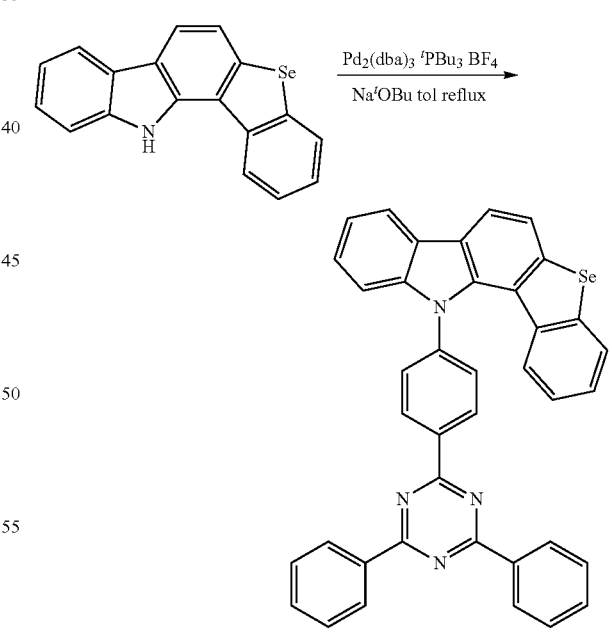

After the chemical reaction equation, 5.78 g white solid is obtained, a yield is 92%.

It can effectively synthesize thermally activated delayed fluorescent molecular materials by preparing the thermally activated delayed fluorescent molecular material according to the preparation method of the present embodiment, while improving synthesis efficiency.

In order to verify whether characteristics of the thermally activated delayed fluorescent molecular material according to the present invention can meet requirements of the electroluminescent device, the thermally activated delayed fluorescent molecular material obtained by the preparation method of the present embodiment is subjected to spectral experiments and photophysical data detection. A fluorescence spectrum as shown in FIG. 1 and the photophysical data as shown in Table 1 are obtained.

Table 1 shows the photophysical data of the thermally activated delayed fluorescent molecular material according to the present invention.

|  | PL Peak (nm) | $S_1$ (eV) | $T_1$ (eV) | $\Delta E_{ST}$ (eV) | PLQY (%) |
|---|---|---|---|---|---|
| Target compound 1 | 486 | 2.91 | 2.77 | 0.14 | 90 |

As shown in FIG. 1, an effective wavelength of the target compound 1 according to the present invention ranges from 400 to 600 nm. Therefore, a luminescence spectrum of the molecule can be adjusted within this range. As can be seen from Table 1, the thermally activated delayed fluorescent molecular material according to the present invention has a smaller energy level difference ($\Delta E_{ST}$) of minimum singlet state and a triplet state.

Figure 2:
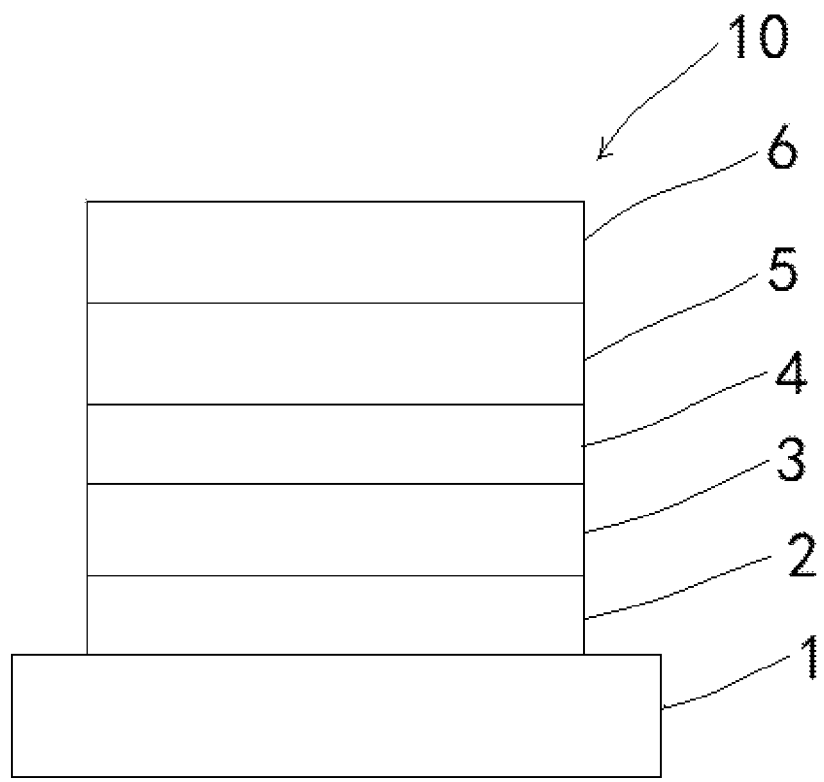
FIG. 2 is a structural view of an electroluminescent device according to an embodiment of the present invention.

As shown in FIG. 2, the present invention also provides an electroluminescent device 10 including the thermally activated delayed fluorescent molecular material.

Specifically, the electroluminescent device includes a first electrode 1, a hole injection layer 2, a hole transport layer 3, a light-emitting layer 4, an electron transport layer 5, and a second electrode 6. The hole injection layer 2 is disposed on the first electrode 1. The hole transport layer 3 is disposed on the hole injection layer 2. The light-emitting layer 4 is disposed on the hole transport layer 3. Material of the light-emitting layer 4 includes the thermally activated delayed fluorescent molecular material and 1,3-bis(9H-carbazol-9-yl)benzene, 11,3-bis(9H-carbazol-9-yl)benzene is a major molecule in which the thermally activated delayed fluorescent molecular material is mixed. The electron transport layer 5 is disposed on the light-emitting layer 4, and the second electrode 6 is disposed on the electron transport layer 5.

In this embodiment, the first electrode 1 is an anode, and material of the first electrode is indium tin oxide. The second electrode 6 is a cathode, and material of the second electrode is one of lithium fluoride or aluminum. Material of the electron transport layer is 1,3,5-tri(3-(3-pyridyl)phenyl)benzene. Material of the hole transport layer is 4,4'-cyclohexylidenebis [N,N-bis(4-methylphenyl)aniline]. Material of the hole injection layer is 2,3,6,7,10,11-hexacyano-1,4,5,8,9,12-hexaazatriphenylene.

Table 2 is a performance data table of the electroluminescent device 10 using the target compound.

| Device | Maximum brightness (cd/m$^2$) | EL peak (nm) | Maximum external quantum efficiency (%) |
|---|---|---|---|
| Containing target compound 1 | 9395 | 488 | 21 |

In the electroluminescent device 10 according to the present invention, the thermally activated delayed fluorescent molecular material is used in the light-emitting layer 4, and efficiently produced the electroluminescent device, thereby improving the luminous efficiency of the electroluminescent device.

The technical scope of the present invention is not limited only to the contents of the description. Those skilled in the art can make various modifications and changes to the embodiments without departing from the spirit and scope of the invention, and such modifications and modifications are within the scope of the invention.

The invention claimed is:
1. A synthesizing method for a thermally activated delayed fluorescent molecular material, comprising steps of:
providing an electron acceptor raw material containing an indenobenzoselenoheteroaromatic ring structure, an electron donor raw material, sodium tert-butoxide, and a catalyst in a reaction container, and pumping and exchanging air in the reaction container with argon, wherein a structure of the electron donor raw material is selected from a group consisting of:

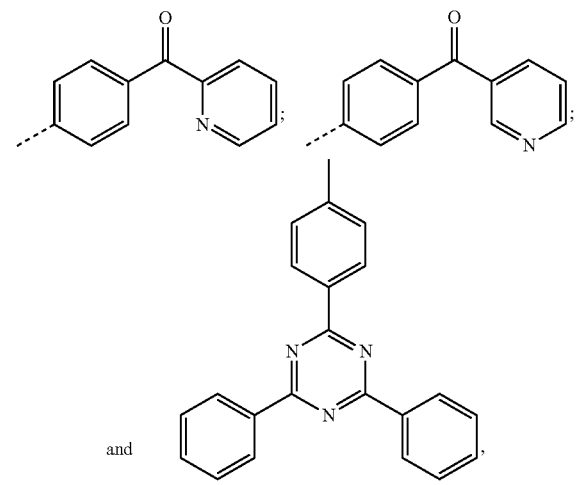

and a structure of the electron acceptor raw material is selected from a group consisting of:

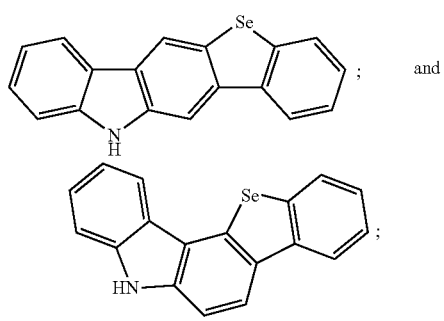

adding a solvent into the reaction container, performing a reflux reaction for 24 hours, and cooling to obtain a first mixed solution;
performing three extractions of the first mixed solution with dichloromethane and three times of water washing, and performing drying with anhydrous sodium sulfate, filtering, and concentrating to obtain a target compound; and performing a column chromatography to the target compound solution by using silica gel having 200 to 300 meshes, and rinsing with an eluent, and finally isolating and purifying to obtain the thermally activated delayed fluorescent molecular material.

2. The synthesizing method for the thermally activated delayed fluorescent molecular material according to claim 1, wherein the donor group raw material is 12H-phenyl[4,5]selenophene [3,2-a]carbazole;

the acceptor group raw material is 2-(4-bromophenyl)-4,6-diphenyl-1,3,5-triazine;

the catalyst comprises tris(dibenzylideneacetone)dipalladium and tri-tert-butylphosphine tetrafluoroborate;

a molar ratio of the donor group raw material, the acceptor group raw material, and the sodium tert-butoxide is 2:2:5;

a molar ratio of the tris(dibenzylideneacetone)dipalladium to the tri-tert-butylphosphine tetrafluoroborate is 1:4;

the solvent is anhydrous toluene; and the eluent is petroleum ether and dichloromethane.

\* \* \* \* \*